(12) United States Patent
Kennedy et al.

(10) Patent No.: US 10,123,789 B1
(45) Date of Patent: Nov. 13, 2018

(54) VARIABLE COMPRESSIBLE WOUND CLOSURE DEVICE AND METHOD

(71) Applicants: James Woodfin Kennedy, Chattanooga, TN (US); Donald Edgar Barker, Signal Mountain, TN (US)

(72) Inventors: James Woodfin Kennedy, Chattanooga, TN (US); Donald Edgar Barker, Signal Mountain, TN (US)

( * ) Notice: Subject to any disclaimer, the term of this patent is extended or adjusted under 35 U.S.C. 154(b) by 1119 days.

(21) Appl. No.: 14/466,249

(22) Filed: Aug. 22, 2014

(51) Int. Cl.
*A61M 35/00* (2006.01)
*A61B 17/00* (2006.01)
*A61M 1/00* (2006.01)
*A61M 27/00* (2006.01)
*A61F 13/00* (2006.01)
*A61F 13/02* (2006.01)

(52) U.S. Cl.
CPC .............. *A61B 17/0057* (2013.01); *A61B 2017/00659* (2013.01)

(58) Field of Classification Search
CPC ........ A61M 35/00; A61M 1/00; A61M 27/00; A61F 13/00; A61F 13/02
See application file for complete search history.

(56) References Cited

U.S. PATENT DOCUMENTS

| | | | | |
|---|---|---|---|---|
| 5,549,584 | A * | 8/1996 | Gross | A61M 1/0088 604/313 |
| 7,569,742 | B2 * | 8/2009 | Haggstrom | A61F 13/0203 128/888 |
| 7,700,819 | B2 * | 4/2010 | Ambrosio | A61L 27/52 602/41 |
| 8,152,785 | B2 * | 4/2012 | Vitaris | A61M 1/0049 604/304 |

* cited by examiner

*Primary Examiner* — Tatyana Zalukaeva
*Assistant Examiner* — Ilya Treyger
(74) *Attorney, Agent, or Firm* — Stephen J. Stark; Miller & Martin PLLC

(57) ABSTRACT

A variable compressible device is utilized with a vacuum to preferentially close a wound. At least one of a strengthening member which resists compression preferentially in one direction, more so than another direction, or a flute in a layer of the closure device whereby to facilitate preferentially compressing in a direction perpendicular to the flute is provided. When utilized with prior art wound closure techniques, a wound is preferentially pulled shut, in what is believed to be a better manner than prior art devices. Furthermore, the device may be utilized with different wound closure techniques.

7 Claims, 2 Drawing Sheets

US 10,123,789 B1

VARIABLE COMPRESSIBLE WOUND CLOSURE DEVICE AND METHOD

CLAIM OF PRIORITY

This application is a divisional application of U.S. Utility patent application Ser. No. 12/399,328 filed Mar. 6, 2009 which claims the benefit of U.S. Provisional Patent Application No. 61/035,551 filed Mar. 11, 2008, which is incorporated herein by reference in its entirety.

FIELD OF THE INVENTION

The present invention relates to an apparatus and method for closing a wound and possibly treating a wound by applying a member having a variable compressibility along at least two axes to preferentially assist in bringing edges of a wound together for closing the wound and possibly treating the wound as well.

BACKGROUND OF THE INVENTION

A number of methods for treating wounds are available on the market today. Specifically, Blue Sky Medical, believed to now be a division of Smith & Nephew, sells equipment utilized to perform the Chariker-Jeter™ method of wound treatment. However, there are not any specific disclosures in the instructions for utilizing that technology for bringing the wound edges towards closure, i.e., bringing the formerly cut edges back together to contain the internal cavity therein.

Louis Argenta and others, working at Wake Forest, have developed a number of wound treatment devices which have subsequently been licensed to a company known as KCI. Argenta, U.S. Pat. Nos. 5,636,643, 5,645,081, and 7,198,046 are incorporated herein by reference. In KCI's commercial embodiment, a foam sponge is utilized atop a wound which is then covered and suction applied thereto. While this method works well to treat wounds, a perceived problem with this technology is that the sponge is compressed significantly in all directions. The applicant believes the sponge can actually work act against itself as it relates to bringing the edges of a cut opening together for wound closure. Specifically, while the wound edges are pulled toward one another by the sponge along one axes, the sponge is also significantly compressed in a perpendicular direction thereby potentially hindering the edges from coming together.

Accordingly, there is believed to exist a need for an improved wound enclosure device and method of its use.

SUMMARY OF THE INVENTION

It is an object of at least some embodiments of the present invention to provide a wound closure method and device comprising an article that tends to significantly compress when exposed to vacuum more in one direction than another.

It is another object of at least some embodiments of the present invention to provide an article of variable compressible material such as foam incorporating a strengthening member with the article exhibiting different compression qualities in one direction than another.

In accordance with the presently preferred embodiment of the present invention, foam having a lateral direction, longitudinal direction and depth is applied relative to the wound. In the longitudinal direction at least one and possibly a plurality of members such as support members or flutes are provided to provide at least one of more resistance to compression in that direction than in a perpendicular direction and/or facilitate compression in the perpendicular or lateral direction. Upon subjection to vacuum pressure, compression is preferably enhanced in a lateral direction while resistance at least some in a longitudinal direction. This is believed to assist in bringing the edges of the wound closer together while resisting bringing the ends of the wound closer together which is believed to possibly retard the ability to close at least some wounds.

By closing more wounds such as possibly 30% or more, huge savings in expenses across the nation are believed to be likely experienced. The wound closing method and apparatus can be utilized in connection with technology such as that disclosed in the Wake Forest University patent portfolio of patents and/or with other wound treatment techniques such as the Chariker-Jeter™ method employed by Blue Sky or still other methods.

BRIEF DESCRIPTION OF THE DRAWINGS

The particular features and advantages of the invention as well as other objects will become apparent from the following description taken in connection with the accompanying drawings in which.

DETAILED DESCRIPTION OF THE DRAWINGS

Figure 1:
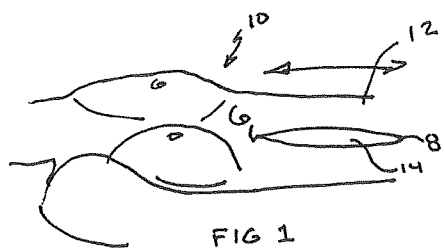
FIG. 1 is a top perspective view of a portion of a patient with an open chest wound.
Figure 2:
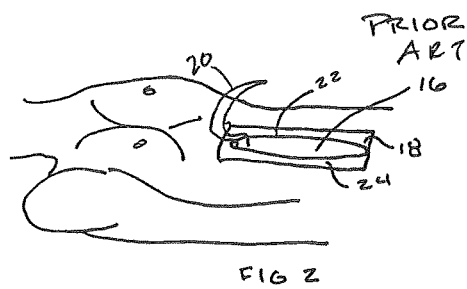
FIG. 2 is a top perspective view of the patient shown in FIG. 1 with a prior art Chariker-Jeter™ wound treatment system connected thereto.

FIG. 1 shows a patient 10 and more particularly a torso area 12 having an open wound 14 therein. FIG. 2 shows what is believed to be a commonly utilized method of treatment namely the Chariker-Jeter™ method. That method normally includes irrigating the wound bed with saline and patting the wound bed 16 dry. A skin sealant is then normally applied to skin that will be covered by the treatment dressing which usually extends at least an inch beyond the wound margin and allowed to dry. Then there are normally two options. Either a single layer of non-adherent gauze cat be cut to the approximate shape and size of the wound bed and laid across wound bed, or if non-adhering gauze is not used, a drain is placed between the saline moistened gauze to create a layer of gauze between the wound bed and the drain. The drain is then normally placed in the wound bed on the gauze since it is preferable in that not to place the drain directly on a wound bed. The gauze is typically saturated with saline. A transparent dressing is then normally placed over the wound bed in contact with at least an inch of the skin beyond the wound edges making sure that the dressing seals against the drain tube. Then a vacuum is normally drawn on the drain tube 20 such as 60 mm, 88 mm or possibly 125 mm or other amount of mercury.

While this certainly is a known effective way to treat a wound 14, there may be problems with bringing the wound edges 22,24 together which is certainly preferred if possible rather than leaving the wound open as illustrated. A closed wound significantly decreases the patient's recovery time and saves resources. An effort believed to assist in bringing wound edges 22,24 together is shown in a device in FIG. 3 in accordance with a presently preferred embodiment of the present invention.

Figure 3:
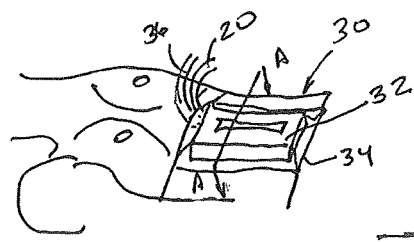
FIG. 3 is a top perspective view showing the use of the applicant's presently preferred embodiment of the present invention in conjunction with the Chariker-Jeter™ system shown in FIG. 2.
Figure 5:
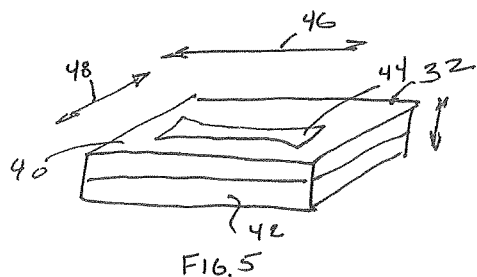
FIG. 5 is a top perspective view of a portion of the variable compressibility wound closure device shown in FIGS. 3 and 4 removed from the patient.

Specifically, in FIG. 3 a variable compression closure device 30 is illustrated perhaps on top of the dressing 18 shown in FIG. 2 with a presently preferred embodiment. The wound closure device 30 shown in this embodiment is shown in further detail in FIGS. 5 and 6. Specifically, the device preferably includes a variable compressible member 32 together with a cover 34 and a connector 36 to provide a vacuum below the cover 34. Cover 34 and connector 36 can take various configurations and designs as are known in the art.

Figure 4:
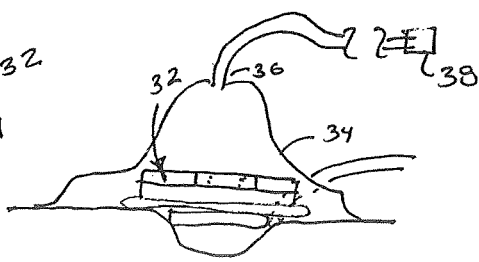
FIG. 4 is a cross section taken along line A-A of FIG. 3.

FIG. 4 shows a cross section taken along the line A-A in FIG. 3 with cover 34 connected to connector 36 which connects to a vacuum supply 38. Vacuum supply could be vacuum as provided from the wall of a hospital room or some other source including a portable vacuum pump or otherwise.

The embodiment of the wound closure member 32 illustrated is a laminated structure having a first layer 40 and second layer 42. First layer 40 is illustrated with a stiffening member 44 as a portion thereof. In the preferred embodiment, the first layer 40 is comprised of a foam such as 450 pores per inch foam or other foam or material possibly may be provided with a cutout disposed towards the middle thereof which receives stiffening member 44 which may be a less compressible member such as a less compressible foam member or possibly even a non-compressible member in some embodiments such as a plastic stiffener or other material.

The stiffening member 44 is preferably constructed in such a way so as to preferentially retard compression more in one direction illustrated as the longitudinal direction 46 while possibly facilitating preferably at least close to normal compression if not enhanced compression in the lateral direction 48. This can be illustrated better with reference to FIG. 6 which shows that if the original dimensions are provided by uncompressed width 50 and length 52. Compressed width 54 is illustrated. When portions of the skin are sutured to the wound edges 24,26 as shown in FIG. 2 outside of the wound 14 are connected to the wound closure member 32, it can be seen that the edges 22,24 are brought closer together than with prior art constructions shown as compressed prior art width 56. Meanwhile, in the length direction 52, the compressed length 58 is preferably longer than the prior art compressed length 60. Otherwise, by compressing the ends 6,8 more towards one another is believed to make the wound edges 22,24 more difficult to close together.

Figure 6:
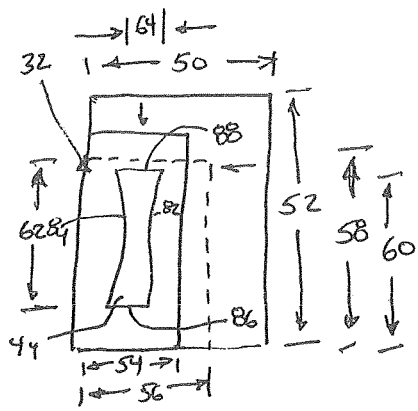
FIG. 6 is a top plan view showing compression of the wound closure device shown in FIGS. 3-5 in comparison to a prior art wound treatment device.

Specifically, a control foam of a small pore was utilized as a control with a length and width of approximately 30 cm and 15 cm respectively. When subjected to pressure as shown in FIG. 4 and FIG. 6 compressed length 60 of 21.5 cm and a compressed width 56 of 7.6 cm. 450 pores per inch foam with a length of 30.6 cm and width of 15.5 cm resulted in a compressed length of 19 cm and a compressed width of 9.2 cm.

A double thickness foam (5 cm thick) having a length of 30.7 cm and a width of 16.3 cm results in a compressed length of 19 cm and a compressed width of 9.7 cm which was similar to the 450 pore per inch foam. Finally, the embodiments shown in FIGS. 3-6 were tested, initially having a length of 30.7 cm and a width of 17.2 cm. After compression, the compressed length 58 was 24.7 and the compressed width 54 was 8. The corrugated construction shown in FIG. 7 initially began at a length of 30.6 cm and a width of 14.2 cm and resulted in a compressed length of 20 cm and a compressed width of 7.6 cm. This embodiment will be discussed in further detail below with reference to FIG. 7. Table 1 provides the results of applicant's testing.

TABLE 1

| | Variable Compressible Foam | | Feb. 9, 2008 | | | | | | |
|---|---|---|---|---|---|---|---|---|---|
| | Size (cm) | | | | | | | | |
| | 0 mm hg pressure | | 125 mm hg pressure | | Delta | | L/W ratio | | |
| | Length | Width | Length | Width | Length | Width | 0 press | 125 press | Delta |
| Sample 1 Small pore control Mm | 30.6 | 15.5 | 21.5 | 7.6 | 9.1 | 7.9 | 1.974 | 2.829 | 1.152 |
| Sample 2 450 ppi foam Mm | 30.6 | 15.5 | 19 | 9.2 | 11.6 | 6.3 | 1.974 | 2.065 | −0.091 |
| Sample 3 Corrugated foam Mm | 30.6 | 14.2 | 20.9 | 7.6 | 9.7 | 6.6 | 2.155 | 2.75 | −0.595 |
| Sample 4 Variable compressible 4.9 cm thick Mm | 30.7 | 17.2 | 24.7 | 8 | 6 | 9.2 | 1.785 | 3.088 | −1.303 |

TABLE 1-continued

| | | Variable Compressible Foam | | | Feb. 9, 2008 | | | | |
|---|---|---|---|---|---|---|---|---|---|
| | | Size (cm) | | | | | | L/W ratio | |
| | | 0 mm hg pressure | | 125 mm hg pressure | | Delta | | | |
| | | Length | Width | Length | Width | Length | Width | 0 press | 125 press | Delta |
| Sample 5 | | | | | | | | | | |
| 5 cm thick | Mm | 30.7 | 16.3 | 19 | 9.5 | 11.7 | 6.8 | 1.883 | 2 | −0.117 |

In addition to conducting compression tests, the applicant also conducted a force test with strain gauges the results of which are provided with four runs of the same material utilized in Table 1 as it relates to sample 1, sample 2, sample 3 and sample 4. Specifically, the ends of the foam pieces were restrained and applied to strain gauges and then subjected to 125 mm of mercury. The variable compressible environment as shown in FIGS. 3-6 provided over three times, and almost four times as much tensile force at the middle of the compressible member 32 than the prior art 450 ppi sponge. Furthermore, when the edges were constrained, the percentage changed in width to the prior art sponge of 450 ppi changed only 27% while the variable compressible 32 changed 56% which is believed to be a significant improvement over the prior art.

Even when doubling the thickness of the 450 ppi foam to a 5 cm control to be comparable in height to that of sample 4, the tension still almost doubled for the improved construction and the width change is still significantly more. These data are believed to translate into more and/or quicker wound closures and hopefully faster patient recovery.

TABLE 2

Foam lateral tension test Date tested Feb. 13, 2008
Raw data
Samples @ 125 mmh @ vac

| | | 450 ppi | Corrugated | 5 cm control | Vari-compress |
|---|---|---|---|---|---|
| Force (gms) | Run 1 | 400 | 531 | 771 | 1180 |
| | Run 2 | 318 | 459 | 761 | 1293 |
| | Run 3 | 365 | 451 | 746 | 1259 |
| | Run 4 | 326 | 469 | 751 | 1192 |
| Avg. (grams) | | 352.25 | 477.5 | 757.25 | 1231 |
| Width at vacuum | | 12.2 | 12 | 12 | 11 |
| Start width | | 15.5 | 14.2 | 16.3 | 17.2 |
| % width change | | 27.05% | 18.33% | 35.83% | 56.36% |

Variable compressible member 32 with stiffening member 44 preferably includes a strengthening member 44 possibly longer in a longitudinal direction 46 and then in a lateral direction 48 as illustrated. In some embodiments it may extend up to the complete length 52, but this is certainly not the case in the embodiments illustrated in FIGS. 5 and 6. Furthermore, there may be more than one strengthening member 44 in some embodiments.

The strengthening member 44 in the presently preferred embodiment is illustrated with a length 62 at least half the length 52 when uncompressed. The width 64 of the strengthening member 44 is illustrated being less than half if not less than one-third or one-quarter the width of uncompressed width 50. Furthermore, although strengthening member 44 is shown only with first layer 40, it may also be included as a portion of layer 42. Strengthening member may extend through layers 40,42. Layers 40,42 may be a single layer in other embodiments with strengthening member 44 utilized therewith in still other embodiments.

Figure 7:
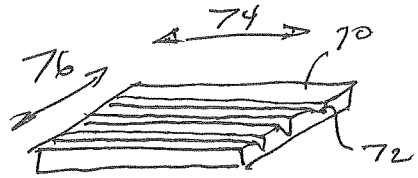
FIG. 7 is a top plan view of an alternative embodiment of a wound closure device.
Figure 8:
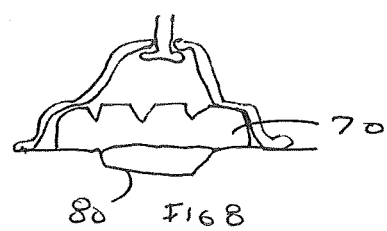
FIG. 8 is a cross sectional view somewhat akin to the view shown in FIG. 4 except using the alternative embodiment of FIG. 7 and a different method of wound treatment than is shown in FIG. 4.

Corrugated foam such as wound closure member 70 shown in FIG. 7 may be a corrugated foam having flute(s) 72 running in the longitudinal direction 74 which is illustrated perpendicular to the lateral direction 76. This embodiment has been found to tend to slightly resist compression in the lengthwise direction but not nearly as significantly as, with the strengthening member 44. However, compression in the width direction was significantly better than the control which provided interesting results. Strengthening member 44 may be combined with flutes 72 which may or may not run the length in the lateral direction 74 of the wound closure member 70. Wound closure member 70 is shown in relationship to a wound bed 80 in FIG. 8 in an uncompressed state.

Although strengthening member 44 as well as flutes 72 which are herein defined is an intentional scoring of material or material removed or that is not otherwise provided in rectangular cross section blocks as has traditionally been provided by prior art constructions.

Figure 9:
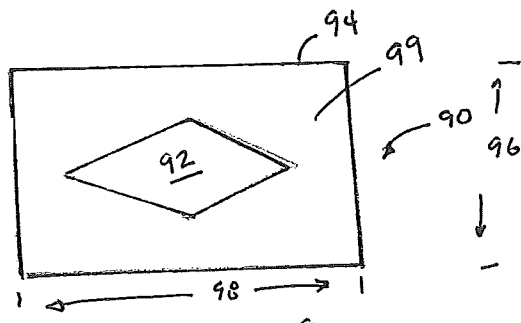
FIG. 9 is a top plan view of a second alternative embodiment of the present invention.

FIG. 9 shows another embodiment of the presently preferred embodiment of the present invention as a closure member 90. Closure member 90 has a flute or cut out 92 disposed internal to a perimeter 94 which is illustrated as being rectangular but could be other shapes in other embodiments. Although a single cut out 19 is illustrated, multiple cutouts could be provided.

Figure 10:
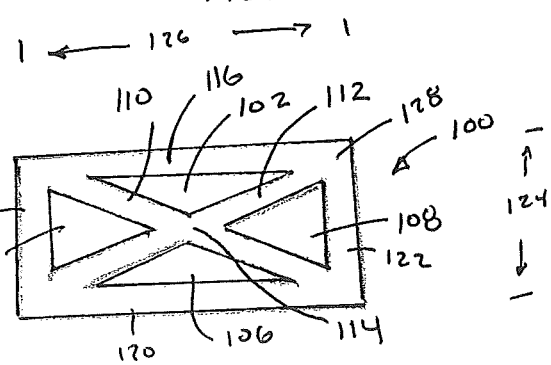
FIG. 10 is a top plan view of a third alternative embodiment of the present invention.

FIG. 10 provides an embodiment of a closure device 100 having a plurality of cutouts 102,104,106,108 which cooperates together to provide somewhat of a scissors or lattice shape comprised of lattice members 110 crossing with lattice member 112 at connection 114. External frame portions 116,118,120,122 may be provided in some embodiments. In other embodiments all or some of the frame members 116,118,120,122 may not be present.

Figure 11:
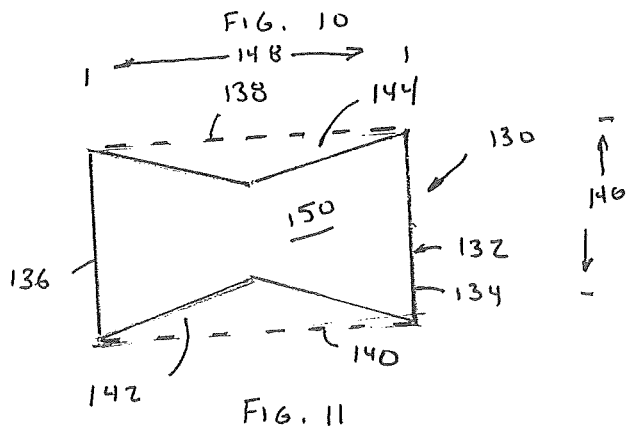
FIG. 11 is a top view of yet another preferred embodiment of the present invention.

Closure device 13 shown in FIG. 11 is such an embodiment. Here a maximum outer perimeter 132 is defined by sides 134,136,138 and 140. Flutes or cutouts 142,144 extend into the maximum outer perimeter 132 by providing flutes or cutouts 142,144 internal to a maximum outer perimeter 132 which is a rectangular shape extending a maximum width 146. It would be obvious to those of ordinary skill in the art that the compressibility and the width direction 146 would be facilitated as opposed to the length direction 148.

This capability is believed to be true for the closure device embodiment 90 of FIG. 9 which should be preferentially compressed in the width direction 96 as opposed to the length direction 98. Similarly, the closure device embodiment 100 should be preferentially compressed in the width direction 124 as opposed to length direction 126. In these embodiments, compressibility may be enhanced with cutouts 92,102,104,106,108,142 and/or 144. In still other embodiments, some or all of the cutouts 92,102,104,106, 108,142 and/or 144 may be filled with foam or other material having a different compressibility than the foam bodies 99,128 and/or 150 of the various embodiments. As illustrated, the cutouts 92,102,104,106,108 and 140,142,144 may or may not extend all the way through a depth (the direction into the page) of the devices 90,100 and 130. Other numbers and shapes of cutouts 92,102,104,106,108, 142 and/or 144 may be provided with other embodiments.

Referring back to FIG. 106, strengthening members 44 may take on various shapes including, but not limited to those having concave sides 82,84 or not in various embodiments. Ends 86,88 may also be concave or not in various embodiments.

All the strengthening materials 44 illustrated as separate components in still other embodiments it may be that foam or other material can be produced in such a manner that compressibility over a portion of the material is changed so that the compressibility of the foam or other material preferentially compresses a width or lateral direction as opposed to a length direction as compared to prior art constructions. In still other embodiments, preferential compression may be obtained in or relative to the depth direction as well.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method of facilitating wound closure comprising:
  (a) providing a cover covering a wound and adapted to maintain a reduced pressure at a site of the wound;
  (b) providing a vacuum supply connected to the cover, said vacuum supply cooperating with the cover to supply the reduced pressure at the site of the wound;
  (c) providing a variable compressible member located between the cover and the wound and having a length, a width and a depth, said variable compressible member having a compressible first layer extending a depth above the wound between the wound and the cover and at least one of a flute and a cutout extending a depth along the length direction into the variable compressible member internal to a maximum outer perimeter extending around the length and the width, said at least one of the flute and the cutout preferentially enhances compression of the variable compressible member in a width direction relative to the length direction under the reduced pressure to thereby enhance closing forces in the width direction applied to the wound in a predetermined manner with the application of the reduced pressure by the vacuum supply.

2. The method of claim 1 further comprising at least one of a dressing and a drain between the variable compressible member and the wound, said drain draining fluid from under the cover.

3. The method of claim 1 wherein the variable compressible member further comprises a second compressible layer connected to and located below the first layer.

4. The method of claim 1 wherein a maximum compressed length under the reduced pressure of the variable compression device is no more than 75% of an uncompressed length.

5. The method of claim 4 wherein the maximum compressed length under the reduced pressure of the variable compression device is no more than about 80% of the uncompressed length.

6. The method of claim 1 wherein the cutouts provided extend through the depth of the first layer.

7. The method of claim 1 wherein said provided flute at least partially retards compression of the first layer in a direction parallel to the flute under the reduced pressure.

\* \* \* \* \*